United States Patent [19]

Matthews et al.

[11] Patent Number: 5,041,078
[45] Date of Patent: Aug. 20, 1991

[54] PHOTODYNAMIC VIRAL DEACTIVATION WITH SAPPHYRINS

[75] Inventors: J. Lester Matthews; Millard M. Judy; Joseph T. Newman; Frank Sogandares-Bernal, all of Dallas; Jonathan L. Sessler, Austin; Anthony Harriman, both of Austin, all of Tex.; Bhaskar G. Maiya, Hyderabad, India

[73] Assignees: Baylor Research Foundation, a nonprofit corporation of the State of Texas, Dallas; Board of Regents, The University of Texas System, Austin, both of Tex.

[21] Appl. No.: 454,300

[22] Filed: Dec. 21, 1989

Related U.S. Application Data

[63] Continuation-in-part of Ser. No. 320,293, Mar. 6, 1989, Pat. No. 4,935,498.

[51] Int. Cl.$^5$ ............................................ A61M 37/00
[52] U.S. Cl. ........................................ 604/4; 540/145
[58] Field of Search .......................................... 604/4–6, 604/20, 403, 408, 416; 540/145

[56] References Cited

U.S. PATENT DOCUMENTS

| | | | |
|---|---|---|---|
| 4,878,891 | 11/1989 | Millard | 604/5 |
| 4,883,790 | 11/1989 | Levy et al. | 540/145 |
| 4,915,683 | 4/1990 | Sieber | 604/4 |
| 4,935,498 | 6/1990 | Sessler et al. | 540/465 |

FOREIGN PATENT DOCUMENTS

| | | |
|---|---|---|
| 0111418 | 6/1984 | European Pat. Off. ............... 604/4 |
| 0196515 | 10/1986 | European Pat. Off. . |
| 0233701 | 8/1987 | European Pat. Off. . |

OTHER PUBLICATIONS

Harriman et al., J. Chem. Soc., Chem. Commun., (1989) 314–316.
Sessler et al., Chem. Abst., vol. 111:125716e (2 Oct. 1989).
Sessler et al., J. Amer. Chem. Soc., 110(16):5586–5588 (1988).
M. J. Broadhurst et al., 18- and 22-$\pi$-Electron Macrocycles Containing Furan, Pyrrole, and Thiophen Rings, Chemical Communications, 1969 pp. 1480–1482.
M. J. Broadhurst et al., The Synthesis of 22 $\pi$-Electron Macrocycles, Sapphyrins and Related Compounds, J. Chem. Soc. Perkin I, 1972, 2111.
Tobin J. Marks et al., Large Metal Ion-Centered Template Reactions, Chemical and Spectral Studies of the "Superphthalocyanine" Dioxocyclipentakis (1-Iminoisoindolinato) Uranium(VI) and Its Derivatives, American Chemical Society 1978.
Edward A. Cuellar et al., Synthesis and Characterization of Metallo and Metal-Free Octaalkylphthalocyanines and Uranyl Decaalkylsuperphthalocyanines[1]. Inorg. Chem. 1981, 20, 3766–3770.
Victor J. Bauer et al., Sapphyrins: Novel Aromatic Pentapyrrolic Macrocycles. J. Am. Chem. Soc. 1983, 105, 6429–6436.
Hans Rexhausen et al., The Synthesis of New 22 $\pi$-Electron Macrocycle: Pentaphyrin. Chem. Soc., Chem. Commun., 1983.

Primary Examiner—C. Fred Rosenbaum
Assistant Examiner—Sharon Rose
Attorney, Agent, or Firm—Arnold, White & Durkee

[57] ABSTRACT

The present invention demonstrates a method of photodynamic inactivation of viruses having a membranous envelope, such as Herpes simplex type 1 and Human immunodeficiency type 1 viruses. The method uses substituted sapphyrin compounds to effect viral deactivation during radiation with light at or near the absorption wavelength of the sapphyrin compound. A highly reactive species selectively toxic to infectious agents is produced.

One particular sapphyrin compound useful for the practice of the invention is 8,17-bis(carboxymethyl)-3,12,13,22-tetraethyl-2,7,18,23-tetramethylsapphyrin (Sapphyrin 2). The most preferred sapphyrin sapphyrin compound for the practice of the invention is 3,8,12,13,17,22-hexaethyl-2,7,18,23-tetramethylsapphyrin (Sapphyrin 1).

The method is particularly suitable for inactivation of viruses in blood and blood products.

33 Claims, 12 Drawing Sheets

1. R = CH$_3$
2. R = CO$_2$H

1. R = CH₃
2. R = CO₂H

PHOTODYNAMIC VIRAL DEACTIVATION WITH SAPPHYRINS

This application is a continuation-in-part of the copending application, U.S. Ser. No. 07/320,293, filed Mar. 6, 1989, now U.S. Pat. No. 4,935,498, issued June 19, 1990.

The present patent application is related to two others filed on the same day herewith and having at least one inventor and one assignee in common. These applications which are incorporated by reference herein are entitled: SAPPHYRINS, DERIVATIVES AND SYNTHESES (by Sessler and Cyr Ser. No. 07/454,298) and PHOTODYNAMIC ACTIVITY OF SAPPHYRINS (by Sessler, Maiya and Harriman Ser. No. 07/454,301).

BACKGROUND OF THE INVENTION

The present invention relates to the use of novel sapphyrin compounds as photosensitization agents for the photodynamic inactivation of infectious agents having membranous envelopes. The general photodeactivation method used in this example was developed by the Infectious Disease and Advanced Laser Applications Laboratories of the Baylor Research Foundation, Dallas, Texas and is a subject of a U.S. Pat. No. 4,878,891 filed June 25, 1987 by Millard Monroe Judy, James Lester Matthews, Joseph Thomas Newman and Franklin Sogandares-Bernal (assigned to the Baylor Research Foundation, Dallas, Tex.).

For the sake of clarity and brevity, many of the terms used herein have been abbreviated and are set out in the following table:

TABLE 1

| NAME | ABBREVIATION |
|---|---|
| Hepatitis virus Type B | HBV |
| Non-A, Non-B hepatitis virus | NANB |
| Human lymphototrophic virus type 1 | HLTV-1 |
| Human immunodeficiency virus type 1 | HIV-1 |
| Simian immunodeficiency virus | SIV |
| Herpes simplex virus type 1 | HSV-1 |
| dihematoporphyrin ether | DHE |
| (commercial form) | Photofrin II ® |
| 2,3-diphosphoglycerate | 2,3-DPG |
| Vesicular stomatitis virus | VSV |
| Phosphate buffered saline | PBS |
| Human serum albumin | HSA |
| Sodium dodecylsulphate | SDS |
| Plaque forming unit per mL | PFU/mL |
| L-alpha-phosphatidylcholine | PCC |
| Cholesterol | C |
| Cholesterol to L-alpha-phosphatidylcholine ratio | c/PCC |
| Hematoporphyrin derivative | HPD |
| Mesochlorin (chlorin of mesoporphyrin) | MC |
| Chlorin e6 | CE |
| Micromolar | uM |
| 3,8,12,13,17,22-hexaethyl-2,7,18,23-tetramethylsapphyrin | Sapphyrin 1 |
| 8,17-bis(carboxymethyl)-8,12,13,22-tetraethyl-2,7,18,23-tetramethyl sapphyrin | Sapphyrin 2 |
| Adenosine triphosphate | ATP |
| Vesicular stomatitis virus | VSV |

A reliable method of sterilizing or inactivating infectious agents in blood and its products could significantly decrease the risk of transfusion-related disease. The requirement that integrity and full function of blood elements be maintained after prophylaxis imposes severe restrictions upon sterilization methods. To be viable, any blood purification procedure must operate without introducing undesirable toxins, damaging normal blood components, or inducing the formation of harmful metabolites. In general, this precludes the use of common antiviral systems such as those based on heating, UV irradiation, or purely chemical means. A photodynamic inactivation approach is a promising approach obviating many of these disadvantages.

Alternatively, blood could be collected into dye-coated bags, and irradiated during the normal post-collection sedimentation period. The bags might be plastic or some other suitable material to which the sapphyrin compound would bind without losing its ability to react with molecular oxygen upon irradiation.

In connection with photodynamic inactivation, a porphyrin compound, dihematoporphyrin ether, was studied by Schnipper et al. (Schnipper, L. E., Lewin, A. A., Swartz, M., and Crumpacker, C. S. (1980) "Mechanisms of photodynamic inactivation of herpes simplex viruses," $J.$ $Clin.$ $Invest.$, 65, 432–438), and shown to act as an efficient photosensitizer for the photoinactivation of both cell-free and cell infected enveloped viruses (Skiles, H. M., Judy, M., Newman, J. T. (1987) "photodynamic inactivation of viruses with hematoporphyrin derivatives" $Abstr.$ $of$ $6th$ $Southern$ $Biomedical$ $Engineering$ $Conference$, 1987, 83). It is likely that the success of this procedure derives from the fact that this dye localizes selectively at or near the morphologically characteristic and physiologically essential viral membrane "envelope" (which has no direct counterpart in normal blood elements) and catalyzes the formation of singlet oxygen upon photoirradiation. The singlet oxygen so produced is believed, in turn, to destroy the essential membrane envelope, thus killing the virus and eliminating its infectivity. Photodynamic blood purification procedures, therefore, apparently rely on the use of photosensitizers which localize selectively at viral membranes.

However, "first generation" dyes such as DHE are not ideal and suffer from a number of serious deficiencies. They contain a range of chemical species, are neither catabolized nor excreted rapidly from the body, and absorb poorly in the red part of the spectrum where blood and body tissues are most transparent (van Gemert, M. J. C., Welch, A. J., Amin, A. P. (1986) "Is there an optimal laser treatment for port wine stains?" $Lasers$ $Surg.$ $Med.$ 6, 76–83). Each of these deficiencies can and does have important clinical consequences.

Effective concentrations can and often do vary from preparation to preparation because of the fact that DHE and its analogs do not contain a single chemically well-defined constituent and the active components have yet to be identified with certainty. Significant quantities of these dyes may remain in patients after treatment because they are not rapidly metabolized. In fact DHE is known to localize in the skin and to induce severe and extended photosensitivity in patients (Oseroff, A. R., Ohuoha, D., Ara, G., McAuliffe, D., Foley, J., Cincotta, L. $Proc.$ $Natl.$ $Acad.$ $Sci.$ $USA$, (1986), 83, 9729 and references therein). Finally because the longest wavelength absorption maximum for these dyes falls at 630 nm, most of the incipient energy used is dispersed or attenuated before reaching a blood-borne pathogen. As a result, less of the initial light is available for singlet oxygen production and photodynamic action (van Gemert, M. J. C., Welch, A. J., Amin, A. P. (1986) "Is there an optimal laser treatment for port wine stains?" $Lasers$ $Surg.$ $Med.$ 6, 76-83). Thus the development of photosensitizers absorbing in the 700 nm region is desirable, provided desirable features such as selective localization on pathogens, low dark toxicity, and efficient photosensitization, are maintained.

The photodynamic inactivation of infectious agents using visible light range photosensitizers is emerging as a potential means of sterilizing banked blood and its products (Skiles, H., Judy, M. M., Newman, J. T. (1985) "Photodynamic inactivation of viruses with hematoporphyrin derivatives", *Abstr. Am. Soc. for Microbiol.*, p. 7, A 38; Skiles, H., Judy, M. M., Newman, J. T. (1987) "Photodynamic inactivation of viruses with hematoporphyrin derivatives", *Abstr. of 6th Southern Biomedical Engineering Conference*, 1987, 83; Matthews, J. L., Newman, J. T., Sogandares-Bernal, F., Judy, M. M., Skiles, H. Leveson, J. E., Marengo-Rowe, A. J., Chanh, T. C. (1988) "Photodynamic therapy of viral contaminants with potential for blood banking applications", *Transfusion*, 28, 81-83 (Rapid Communication); Matthews, J. L., Sogandares-Bernal, F., Judy, M. M., Marengo-Rowe, A. J., Skiles, H., Leveson, J., Chanh, T., and Newman, J. (1988) "Photodynamic inactivation of human immunodeficiency virus in human blood", *Transfusion*, 28(S), 31S; Dennis, M. V., Judy, M. M., Matthews, J. L. and Sogandares-Bernal, F. (1989) "Protective qualities of mitochondrial and cytosolic fluorescent dyes against in vitro and in vivo infection by the tulahuen strain of *Trypanosoma cruzi, J. Parasitol.* (Accepted for Publication); Chanh, T., Allan, J., Matthews, J. L., Sogandares-Bernal, F., Judy, M. M., Newman, J. T. (1989) "Photodynamic inactivation of simian immunodeficiency virus in blood", (Accepted for publication by Exp. Virol); Sieber, F. (1988) "Antineoplastic and antiviral properties of merocyanine 540", in SPIE, *Advances in Photochemotherapy* (Edited by H. Tayaba) 997, 128). The enveloped viruses, HIV and its simian analogue (SIV), and HSV-1, all suspended in whole human blood have been inactivated using DHE (Matthews, J. L., Newman, J. T., Sogandares-Bernal, F., Judy, M. M., Skiles, H. Leveson, J. E., Marengo-Rowe, A. J., Chanh, T. C. (1988), "Photodynamic therapy of viral contaminants with potential for blood banking applications", *Transfusion*, 28, 81-83 (Rapid Communication); Chanh, T., Allan, J., Matthews, J. L., Sogandares-Bernal, F., Judy, M. M., Newman, J. T. (1989), "Photodynamic inactivation of simian immunodeficiency virus in blood", (Accepted for publication by Exp. Virol). No measurable changes in red blood cell membrane integrity, 2,3-DPG activity concentration, or in ATP concentration followed photodynamic treatment of whole blood containing 200 ug/ml of DHE (estimated 333 uM macrocycle concentration) (Matthews, J. L., Sogandares-Bernal, F., Judy, M. M., Marengo-Rowe, A. J., Skiles, H., Leveson, J., Chanh, T., and Newman, J. (1988) "Photodynamic inactivation of human immunodeficiency virus in human blood", *Transfusion*, 28(S), 31S). This concentration of DHE is estimated to exceed (by a factor of 10-20) that required for viral inactivation.

In 1985, an estimated 10 million units of whole blood were processed by over 800 blood banks in the U.S. and 14 million units of blood components were transfused. This use reflects major needs for blood components in managing trauma, hemorrhagic and neoplastic disorders, and recipients of bone marrow or solid organ transplants. Use of blood products still involves significant risk to the recipient because of the potential transmission of infectious agents. Among human infections, viruses which are enclosed by a lipid membrane or envelope, such as the hepatitis viruses (HBV and NANB), HLTV-1 (a leukemia virus), and HIV-1 (the AIDS virus), as well as Chagas' disease and malaria can be transmitted by blood transfusion (Cohen, M. D., Munoz, A., Reitz, B. A., et al. (1989) "Transmission of retroviruses by transfusion of screened blood in patients undergoing cardiac surgery", *N. Engl. J. Med.* 320, 1172-1176). Screening of donors and serologic testing reduce the risk, but these precautions still provide insufficient protection as detectable HIV-1 antibody may not be present during the early stage of infection (Cohen, M. D., Munoz, A., Reitz, B. A., et al. (1989) "Transmission of retroviruses by transfusion of screened blood in patients undergoing cardiac surgery", *N. Engl. J. Med.* 320, 1172-1176).

In a number of prior studies on photodynamic inactivation of viruses and protozoan infectious agents in blood (Skiles, H., Judy, M. M., Newman, J. T. (1985) "Photodynamic inactivation of viruses with hematoporphyrin derivatives", *Abstr. Am. Soc. for Microbiol.*, p. 7, A 38; Skiles, H., Judy, M. M., Newman, J. T. (1987) "Photodynamic inactivation of viruses with hematoporphyrin derivatives", *Abstr. of 6th Southern Biomedical Engineering Conference*, 1987, 83; Matthews, J. L., Newman, J. T., Sogandares-Bernal, F., Judy, M. M., Skiles, H. Leveson, J. E., Marengo-Rowe, A. J., Chanh, T. C. (1988) "Photodynamic therapy of viral contaminants with potential for blood banking applications", *Transfusion*, 28, 81-83 (Rapid Communication); (Matthews, J. L., Sogandares-Bernal, F., Judy, M. M., Marengo-Rowe, A. J., Skiles, H., Leveson, J., Chanh, T., and Newman, J. (1988) "Photodynamic inactivation of human immunodeficiency virus in human blood", *Transfusion*, 28(S), 31S; Dennis, M. V., Judy, M. M., Matthews, J. L. and Sogandares-Bernal, F. (1989) "Protective qualities of mitochondrial and cytosolic fluorescent dyes against in vitro and in vivo infection by the tulahuen strain of *Trypanosoma cruzi, J. Parasitol.* (Accepted for Publication); Chanh, T., Allan, J., Matthews, J. L., Sogandares-Bernal, F., Judy, M. M., Newman, J. T. (1989) "Photodynamic inactivation of simian immunodeficiency virus in blood." (Accepted for publication by Exp. Virol). Photofrin II ® and excitation with 630 nm light were used. Blood appreciably absorbs as well as scatters light in the wavelength region <630 nm (e.g. see FIG. 1 of van Gemert et al. 1986), and it exhibits a broad relative absorption minimum at approximately 680 nm. Therefore, efficient photosensitizers absorbing in the longer red wavelength region potentially offer more efficient use of excitation light energy. Photophysical measurements of Maiya, B. G., Cyr, M., Harriman, A., and Sessler, J. L. (1989) "In-vitro photodynamic activity of diprotonated sapphyrin: a 22 pi-electron pentapyrrolic porphyrin-like macrocycle", (Submitted to *J. Phys. Chem.*) have shown that the triplet state of decaalkylsaphyrin macrocycle (FIG. 1, Structure 1) in monomer form efficiently generates singlet oxygen ($Phi_{delta}=0.25$ $CH_3OH$). As the sapphyrins also exhibit extinction coefficients in the range of $1\times10^4 cm^{-1}$ at wavelengths near 680 nm (See FIG. 2) and offer potential as long wavelength photosensitizers, the photodynamic inactivation of cell-free, enveloped HSV-1 using the free-base sapphyrin (FIG. 1, Structure 1) and its dicarboxyl functionalized analogue (FIG. 1, Structure 2) was studied. In order to assess qualitatively their degree of monomerization and to identify the viral binding environment of the photosensitizer, fluorescence measurements were made of these sapphyrins dissolved in solvents of different polarity or in the presence of liposomes, human plasma proteins, and cell-free VSV (also an enveloped virus).

Consequently, the present inventors have discovered that sapphyrins are effective photosensitizers for the photo-eradication of cell-free viruses, and especially cell-free HIV-1. The sapphyrin compounds are new and no sapphyrins have been used for this purpose before. One of the sapphyrins tested is the single most effective substance yet found for the photodynamic eradication of the AIDS virus, being twice as efficient on a normalized per macrocycle incident unit of light basis as the current best available dye, DHE.

SUMMARY OF THE INVENTION

The present invention involves a method of photodynamic inactivation of infectious agents using the novel class of sapphyrin compounds as photosensitizers to produce a highly reactive species selectively toxic to particular infectious agents. In particular, the method is applicable to the inactivation of viruses having a membranous envelope. In a most preferred embodiment, the method is used to inactivate viruses in blood.

The method is effective in the inactivation of enveloped viruses exemplified by Herpes simplex virus type 1 and vesicular stomatis virus. The method is particularly effective in the inactivation of human immunodeficiency virus type 1.

One particular sapphyrin compound useful for the practice of the invention is 8,17-bis(carboxymethyl)-3,12,13,22-tetraethyl-2,7,18,23-tetramethylsapphyrin (Sapphyrin 2). The most preferred sapphyrin compound for the practice of the invention is 3,8,12,13,17,22-hexaethyl-2,7,18,23-tetramethylsapphyrin (Sapphyrin 1).

DETAILED DESCRIPTION OF PREFERRED EMBODIMENTS

Figure 1:
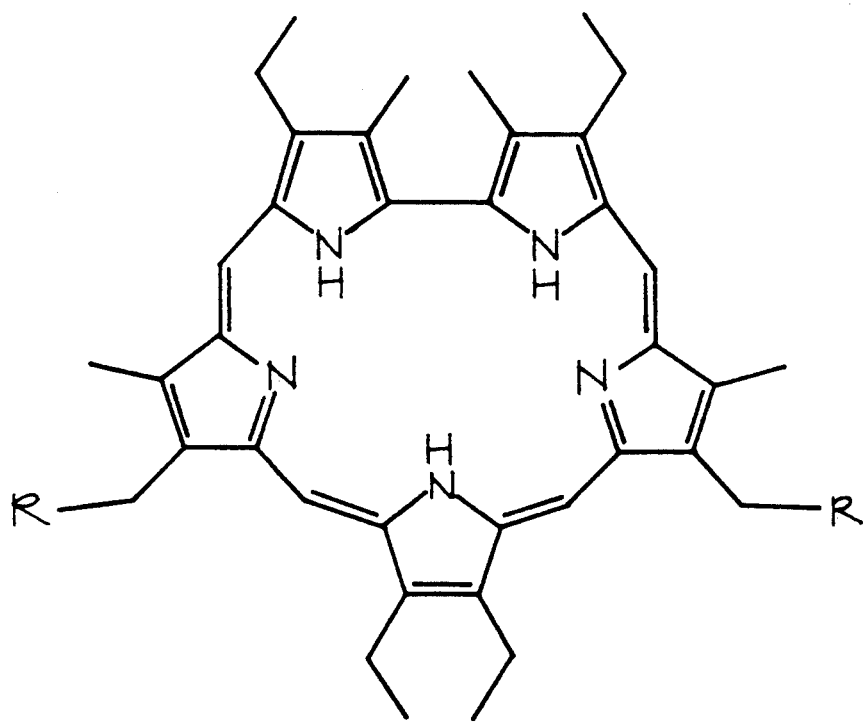
FIG. 1 shows the structures of sapphyrin photosensitizers used in this study.
Figure 2:
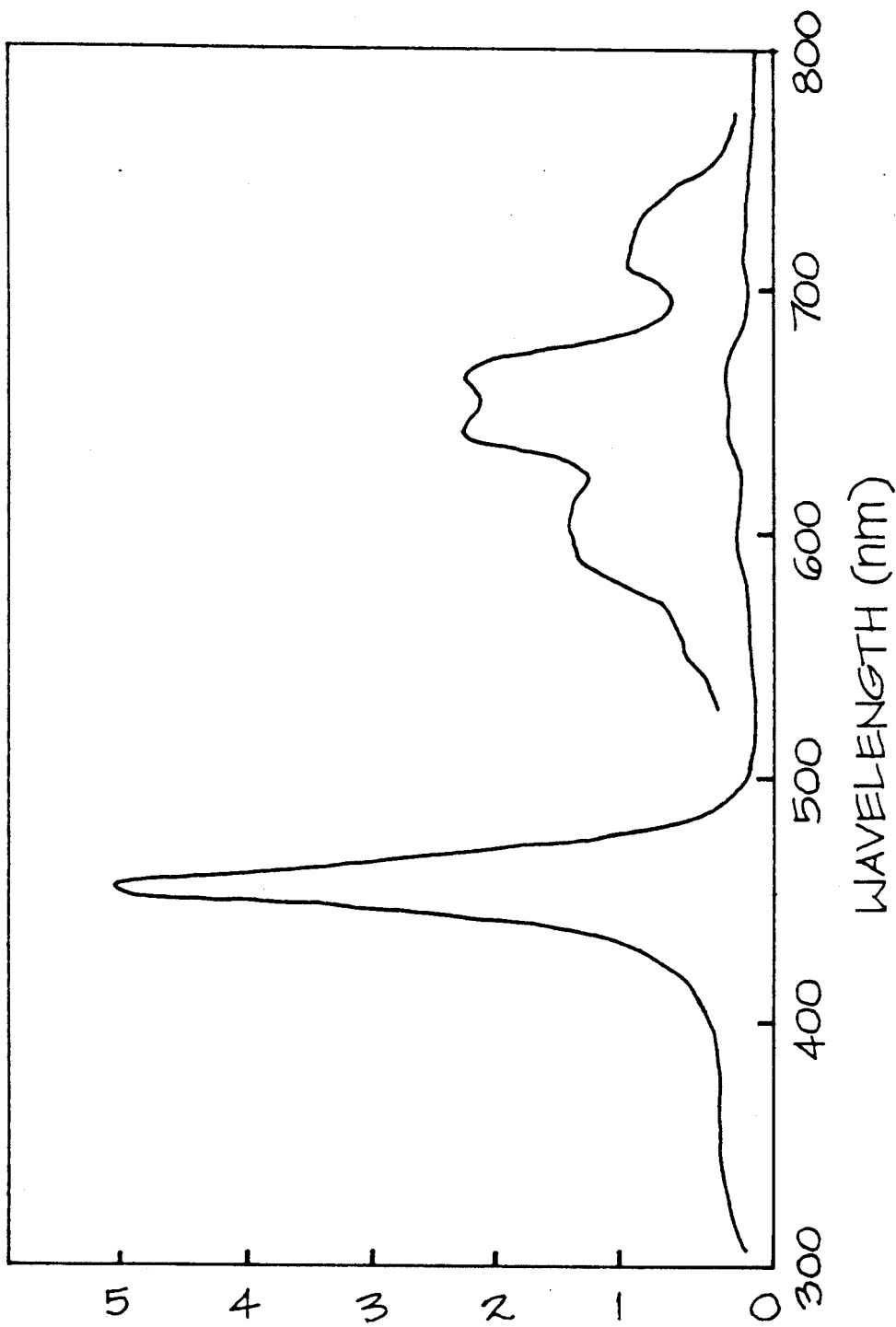
FIG. 2 shows the absorption spectrum of a 3.5 uM solution of the decaalkyl sapphyrin 1 in $CHCl_3$.
Figure 3A:
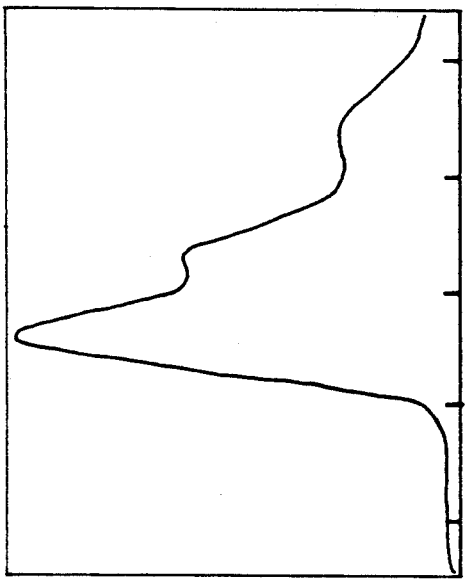
FIG. 3 shows normalized emission spectra of the decaalkyl sapphyrin 1 in $CHCl_3$. The excitation wavelengths were 455 nm, 440 nm, 440 nm, and 420 nm for spectra a, b, c, and d, respectively; the total macrocycle concentrations for these four experiments were 0.37 uM, 0.9 um, 3.3 uM, and 3.3 uM, respectively. The peaks marked with an asterisk are due to dimer bands.
Figure 3B:
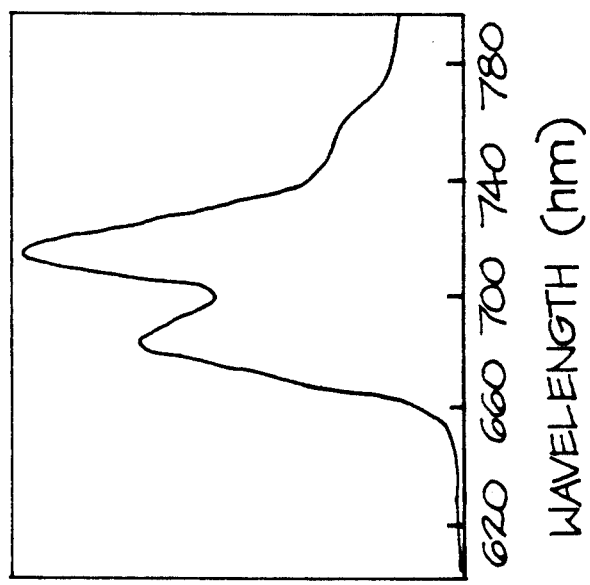
Figure 3C:
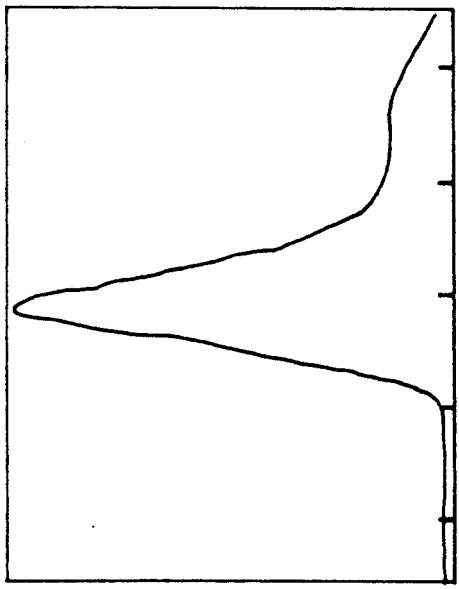
Figure 3D:
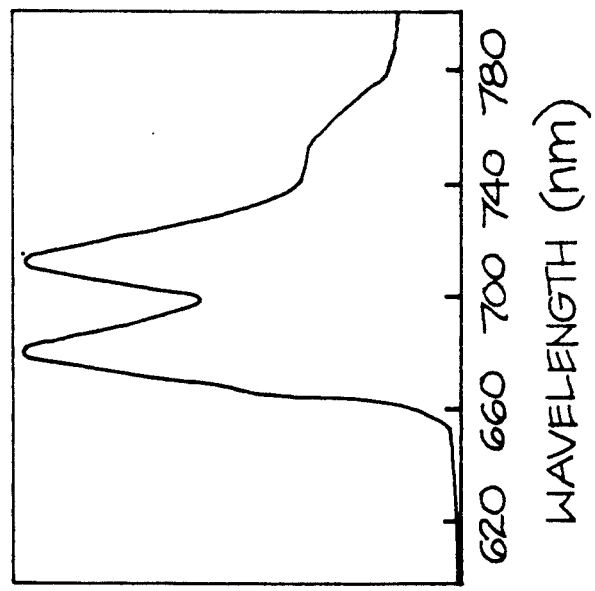

Photosensitizers. Sapphyrin 1 (3,8,12,13,17,22-hexaethyl-2,7,18,23-tetramethylsapphyrin) and the dicarboxy functionalized analogue (compound 2) (8,17-bis(- carboxymethyl)-3,12,13,22-tetraethyl-2,7,18,23-tetramethylsapphyrin) were synthesized using improvements of the methods of Bauer, V. J., Clive, D. L. J., Dolphin, D., Paine, J. B. III, Harris, F. L., King, M. M., Loder, J., Wang, S.-W. C., Woodward, R. B. (1983) "Sapphyrins: Novel aromatic pentapyrrolic macrocycles", *J. Am. Chem. Soc.* 105, 6429–6436. Sapphyrin 1 was used directly in its neutral unprotonated form or converted to its more stable dihydrochloride salt. Under the aqueous conditions prevailing in our experiments (PBS, pH =7.3), both starting sapphyrin species are expected to be in their neutral form represented by structure !. All biological and spectroscopic results obtained were consistent with this supposition. In aqueous medium at pH 7.3, sapphyrin 2 is expected to be in its dianionic (dicarboxylate) form. Stock solutions of the compounds with concentration in the range of 2–3 mg/ml were stored at −75° C. in the dark. Solutions containing the compounds were prepared daily for use; excess solutions were discarded daily.

Reagents. All solvents (Sigma, Aldrich) were of HPLC grade and used as received. HSA containing <0.005% fatty acids, PCC, SDS and C (all from Sigma) were used as received.

Fluorescence Spectra. Fluorescence emission or excitation spectra were obtained on either a Perkin Elmer Model LS-5 spectrofluorometer an SLM-Aminco SPF-500C spectrofluorometer.

Viruses. Herpes simplex type 1 (HSV-1) was propagated in Vero (African Green Monkey Kidney) cells. Cell-free viral suspensions were obtained by freeze-thaw cycles followed by low speed centrifugation to remove cell debris. These suspensions contained $10^5$–$10^7$ PFU/ml and were diluted to $1\times10^6$ PFU/ml for photodynamic treatment.

Vesicular stomatitis virus was kindly provided by Dr. Stuart Nichol, Department of Microbiology, University of Nevada School of Medicine, Reno, Nev. The virus was propagated in monolayer cultures of BHK-2I cells cultured at 37° C. in MEM medium supplemented with 5% bovine serum. The supernatants were harvested and clarified by low speed centrifugation followed by high speed ultracentrifugation to pellet the released virus particles. Virus pellets were then resuspended in TEN buffer, layered onto 5 to 40% sucrose gradient and banded by centrifugation. Purified virus bands were pooled, eluted with TEN buffer and pelleted to remove sucrose and concentrated. Virus pellets were resuspended in PBS buffer and protein concentrations determined using a Pierce BCA assay system. Virus protein concentrations were usually about 2 mg/ml of PBS buffer. All steps were carried out at 4° C. After the final wash, the viruses were suspended in MEM at $1\times10^9$ PFU/ml, (0.1 ml total volume), frozen at liquid nitrogen temperature, packaged over solid $CO_2$ and shipped. After receipt, the frozen samples were stored at −75° C. prior to quick thawing and dilution in PBS, pH 7.3, in preparation for the fluorescence and sapphyrin binding studies.

Photosensitization studies. Measurements of the photodynamic inactivation of HSV-1 with sapphyrins 1 and 2 were done using two different fluid containment systems and light sources. In those measurements, the viral suspension (1 ml volume) was held stationary in a glass test tube and exposed to light from an Argon pumped DCM dye laser (680 nm wavelength). The uniformity of the incident light intensity upon the lateral surface of the liquid volume was increased by collecting the dye laser beam with a silica optical fiber and imaging the output end of the fiber upon the sample (Skiles, H. M., Judy, M., Newman, J. T. (1987) "Photodynamic inactivation of viruses with hematoporphyrin derivatives" *Abstr. of 6th Southern Biomedical Engineering Conference*, 1987, 83). Irradiance at the sample surface was 47.75 mW/cm$^2$ and exposure of 10 J/cm$^2$ was used. In companion measurements, the viral suspension was pumped (small flow rate=$2\times10^{-2}$ ml/min) through a transparent tube arranged in multiple planar loops as described in previous HSV-1 and HIV-1 studies (Matthews, J. L., Newman, J. T., Sogandares-Bernal, F., Judy, M. M., Skiles, H. Leveson, J. E., Marengo-Rowe, A. J., Chanh, T. C. (1988) "Photodynamic therapy of viral contaminants with potential for blood banking applications", *Transfusion*, 28, 81–83 (Rapid Communication)). This process was studied in anticipation of the potential use of blood flow during blood bank processing. For the photodynamic inactivation experiments with fluid flow, light from a 1000 W xenon lamp was passed through an IR dichroic mirror and a 680±5 nm interference filter (50% transmission) for the light source and imaged onto the flow cell. An irradiance of 23.8 mW/cm$^2$ and exposure of 10 J/cm$^2$ were used in the flow studies.

For each of the photosensitizer concentrations studied, two samples of each viral suspension had photosensitizer added; one was exposed to light, and the other was held in the dark. A third sample without added photosensitizer was treated only with light, and a fourth without added photosensitizer served as an unilluminated control. Except during irradiation, during which controls also were held at nominal room temperature (22° C.), all manipulations were carried out at 4° C. with minimal exposure to extraneous light.

The efficiency of viral photodynamic inactivation attained with each experimental condition was determined as the percentage of infectivity retained expressed in PFU/ml.

The assay has been described previously (Matthews, J. L., Newman, J. T., Sogandares-Bernal, F., Judy, M. M., Skiles H., Leveson, J. E., Marengo-Rowe, A. J., Chanh, T. C. (1988) "Photodynamic therapy of viral contaminants with potential for blood banking applications", *Transfusion*, 28, 81–83 (Rapid Communication). Briefly, three- to four-day old Vero monolayers in six-well culture plates were infected with treated or control virus suspensions. Treated and untreated viruses were serially diluted in Hank's balanced salt solution without neutral red dye. The growth medium was removed from the monolayers, and 0.2 ml of the appropriate viral dilution was inoculated into duplicate wells. After 1.5 hr adsorption at 37° C., an overlay of equal volumes of 2X strength L-15 medium and 2% methyl-cellulose was added to the monolayers. Following a three-to four-day incubation time at 37° C., the overlay medium was removed; monolayers were fixed with methanol, and stained with Giemsa stain to provide contrast. Plaques were counted using 20X the ratio [PFU/ml (light+dye)]/PFU/ml (dye, no light).

Liposome Binding Assay Unilaminar liposomes were prepared by modification of the method of Stocco, A. W., Goodwin, D., Zakin, D. (1987) "Reconstitution of membrane proteins: sequential incorporation of integral membrane proteins into preformed lipid bilayers", *Biochemistry* 26, 830–839. Basically, the liposomes were prepared by mixing PCC (Sigma #P-5763) and C (Sigma #C-8253) in a glass tube. The solvent was evaporated under a stream of nitrogen and degassed Dulbecco's PBS (DPBS) without $Ca^{++}$ and $Mg.^{++}$ DPBS, pH = 7.3 was added to the lipid film to give a 10 uM concentration. The tube was vortexed vigorously for 5 minutes and then sonicated (Heat Systems Model W225R) in ice. A micro tip was used at a power output of 6, pulsed operation at 50% duty cycle for 7 minutes. At this point, visible clearing of the suspension was apparent and the liposomal suspension was harvested and diluted for fluorescence studies. A fixed concentration of sapphyrin was added to each dilution and held for equilibration at 4° C. for 20 hours.

HSA Binding Assay. HSA as received from Sigma was diluted in PBS, pH=7.3. A fixed amount of sapphyrin was added to each dilution and held at 4° C. for 20 hours before equilibration.

With sapphyrins 1 and 2 present in PBS, at concentrations ranging between 0.1 and 10 uM, no appreciable fluorescence emission could be observed for wavelengths >680 nm or for any excitation wavelength between 300 and 680 nm. Both compounds in aqueous PBS are likely to be essentially completely aggregated, and all fluorescence is likely to be quenched. In contrast, fluorescence spectra were obtained in less polar media with the presence of monomeric and dimeric species manifested respectively in terms of a set of paired emission maxima located near 680 and 755 nm and in terms of a single peak located near 712 nm.

Figure 4:
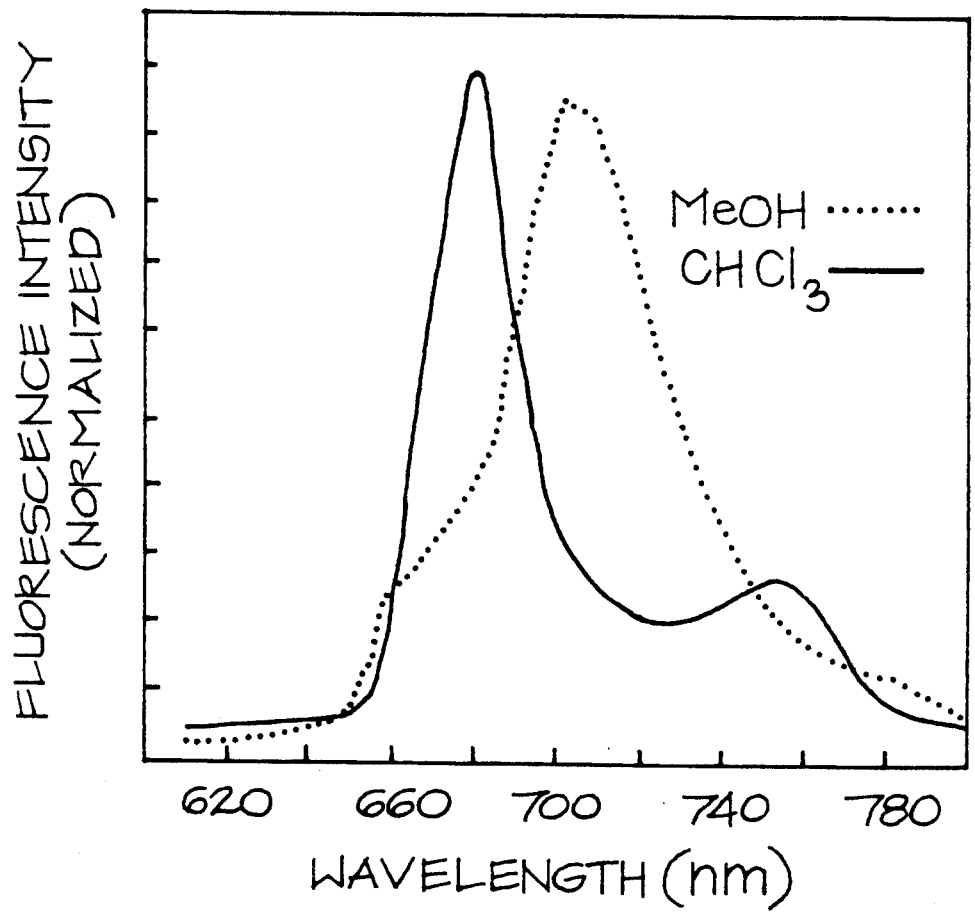
FIG. 4 shows the normalized emission spectra of the decaalkyl sapphyrin 1 in $CHCl_3$ and MeOH. In both cases the total macrocycle concentrations was 0.1 uM and photoexcitation was effected at 440 nm.

Fluorescence emission spectra obtained from $CHCl_3$ solutions of sapphyrin 1 disclosed concentration-dependent dimerization as evidenced by the growth of the 712 nm emission with increasing concentration (FIG. 3). Evidence of enhanced dimerization of sapphyrin 1 in solvents of relatively higher polarity, such as $CH_3OH$ is seen in FIG. 4. Specifically, a clear increase in the 712 nm emission intensity is evident in $CH_3OH$ (epsilon=33.6) as compared to that observed at equal concentration in $CHCl_3$ (epsilon=4.81).

Figure 5:
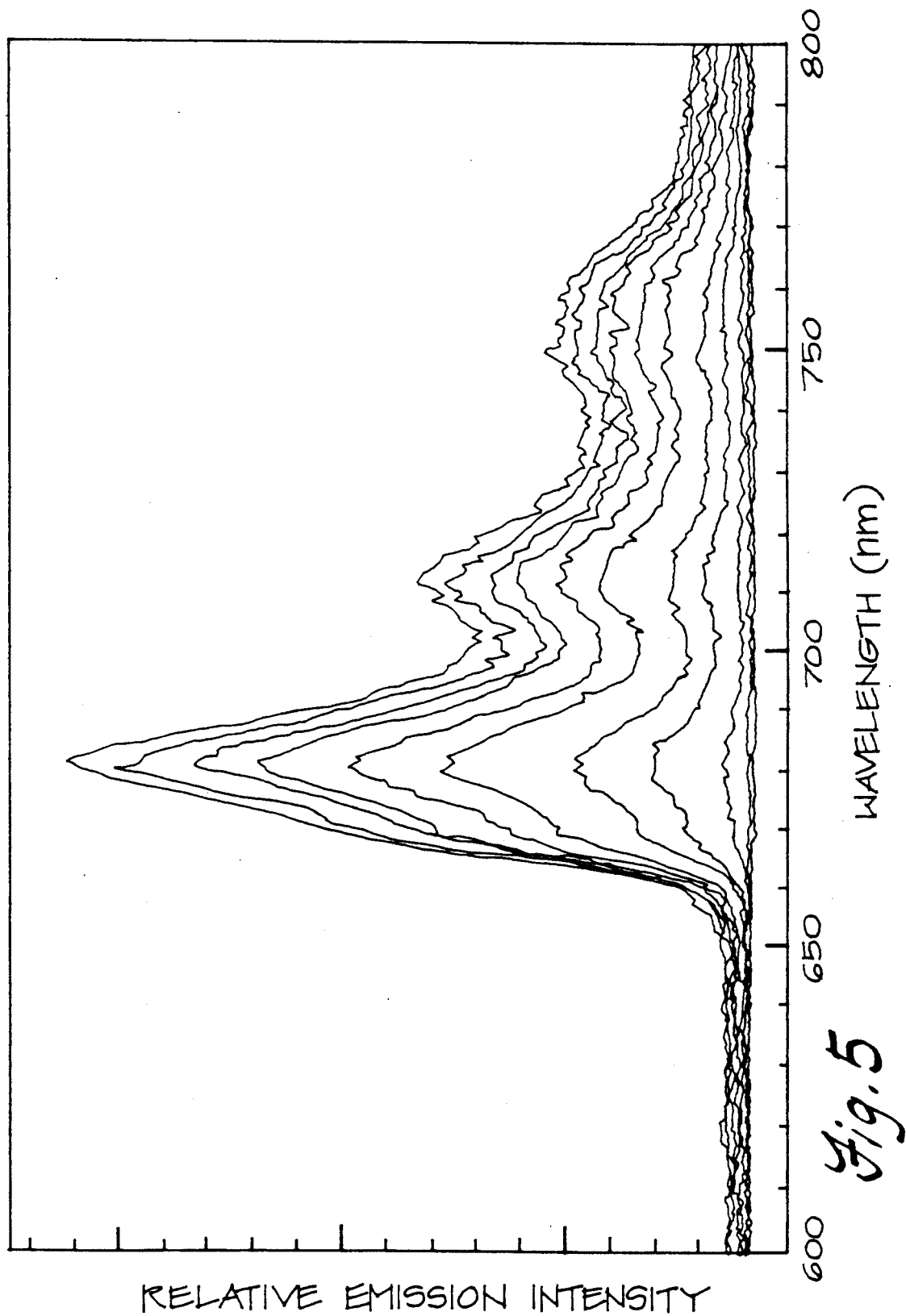
FIG. 5 shows the emission spectra of an aqueous suspension (pH 7.3) of sapphyrin 1 in the presence of liposomes containing 90% L-alpha-phosphatidylcholine and 10% cholesterol. The traces show in order of increasing emission intensity, liposome concentrations of 0,0.1, 1, 5, 10, 25, 75, 100, 150, and 200 uM. In all cases, the total sapphyrin concentration Was held constant at 1.79 uM and excitation was effected at 453 nm.
Figure 6:
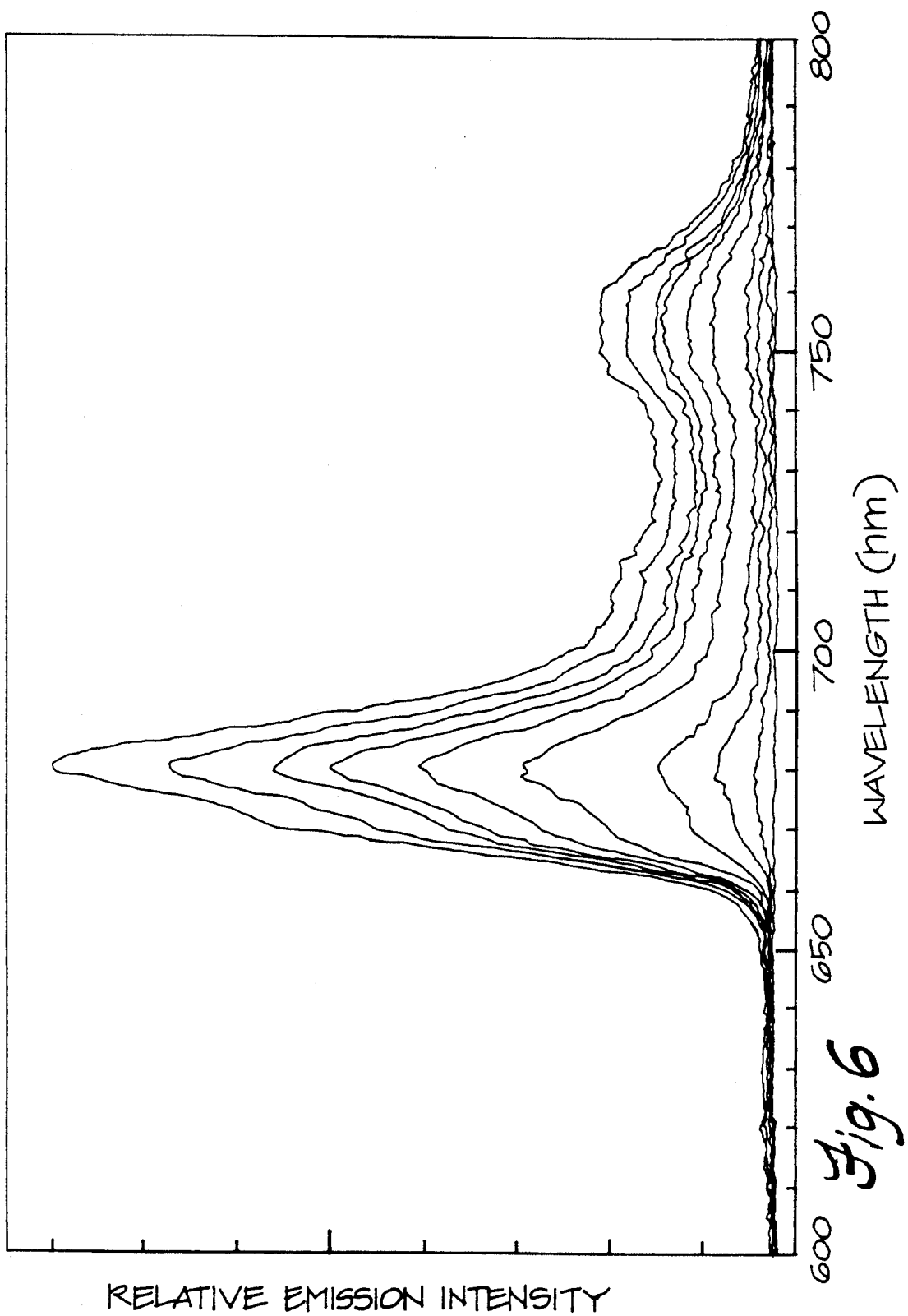
FIG. 6 shows the emission spectra of aqueous suspensions (pH 7.3) of sapphyrin 1 in the presence of liposomes containing 61.5% L-alpha-phosphatidylcholine and 38.5% cholesterol. The traces show in order of increasing emission intensity, liposome concentrations of 0, 0.1, 1, 5, 10, 25, 75, 100, 150, and 200 uM. In all cases, the total sapphyrin concentration was held constant at 1.79 uM and excitation was effected at 453 nm.

Examination of the fluorescence emission spectra of sapphyrin 1 in the presence of liposomes containing different C/PCC values are shown in FIGS. 5 and 6. The presence of appreciable concentrations of both monomer and dimer bound to the liposomes having the relatively lower C/PCC=0.11 value is seen in FIG. 5. In contrast, binding of essentially monomers only by the liposomes containing the higher C/PCC=0.63 value is evidenced in FIG. 6 by the disappearance of appreciable fluorescence intensity due to dimers at 712 nm and the presence of the 680 and 755 nm monomer peaks.

Figure 7:
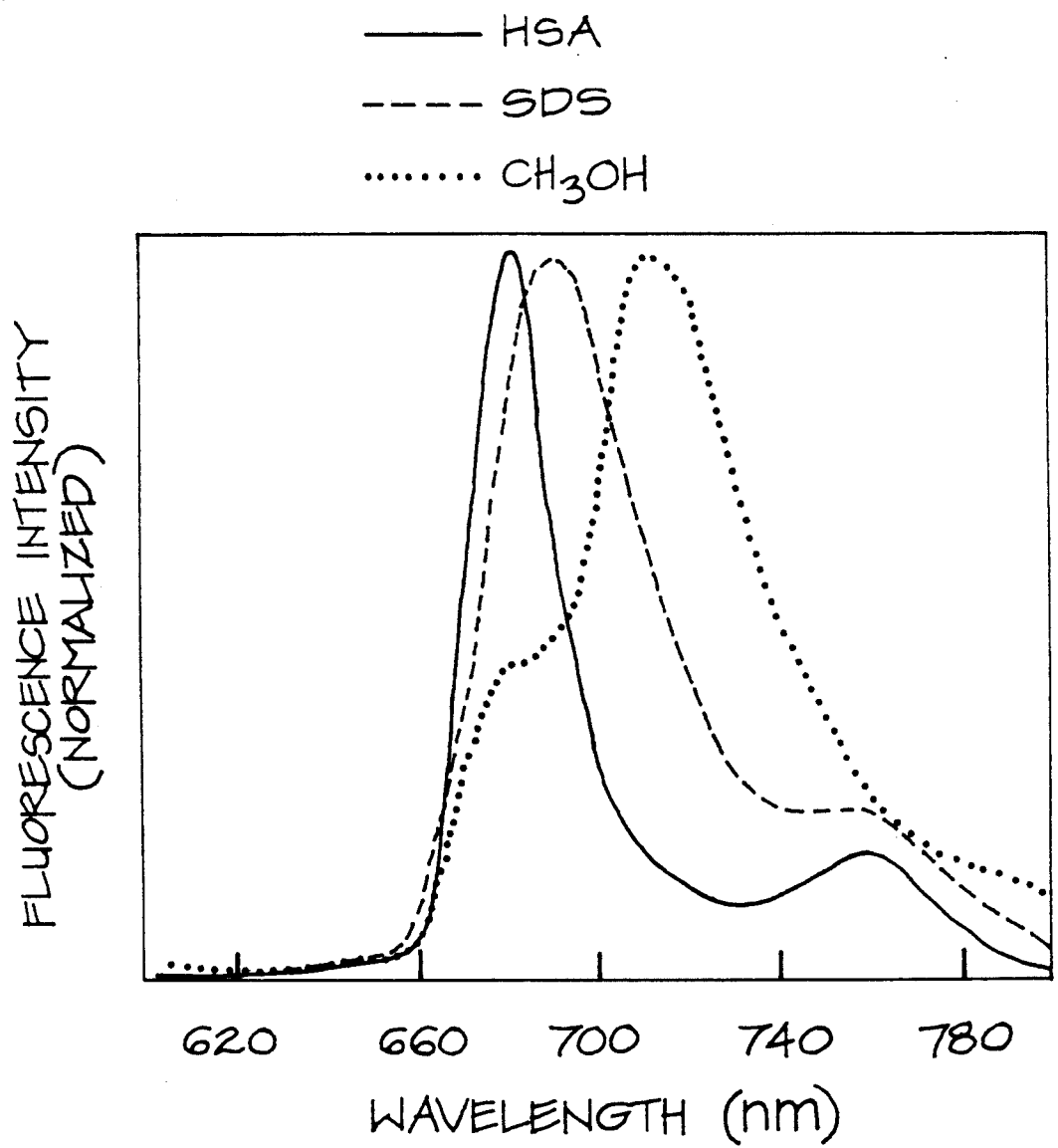
FIG. 7 shows the normalized fluorescence emission spectra of the dicarboxyl substituted sapphyrin 2 in the presence of HSA, SDS, and $CH_3OH$. In all cases, the total sapphyrin concentration was held constant at $5.0 \times 10^{-7}$ M and photoirradiation was effected at 445 nm. Not shown is the corresponding emission profile for 2 in $H_2O$ as no detectable intensity was observed under these conditions.

Fluorescence emission spectra for the dicarboxyl substituted sapphyrin 2 in aqueous HSA and SDS and in $CH_3OH$ are shown in FIG. 7. Dimerization in the relatively polar $CHCl_3$ environment is evidenced by the 712 nm peak. SDS micelles and the binding sites of HSA offer a less polar environment in which the monomer is the dominant form as seen by the presence of the 680 and 755 nm peaks and absence of the 712 nm peak.

Figure 8:
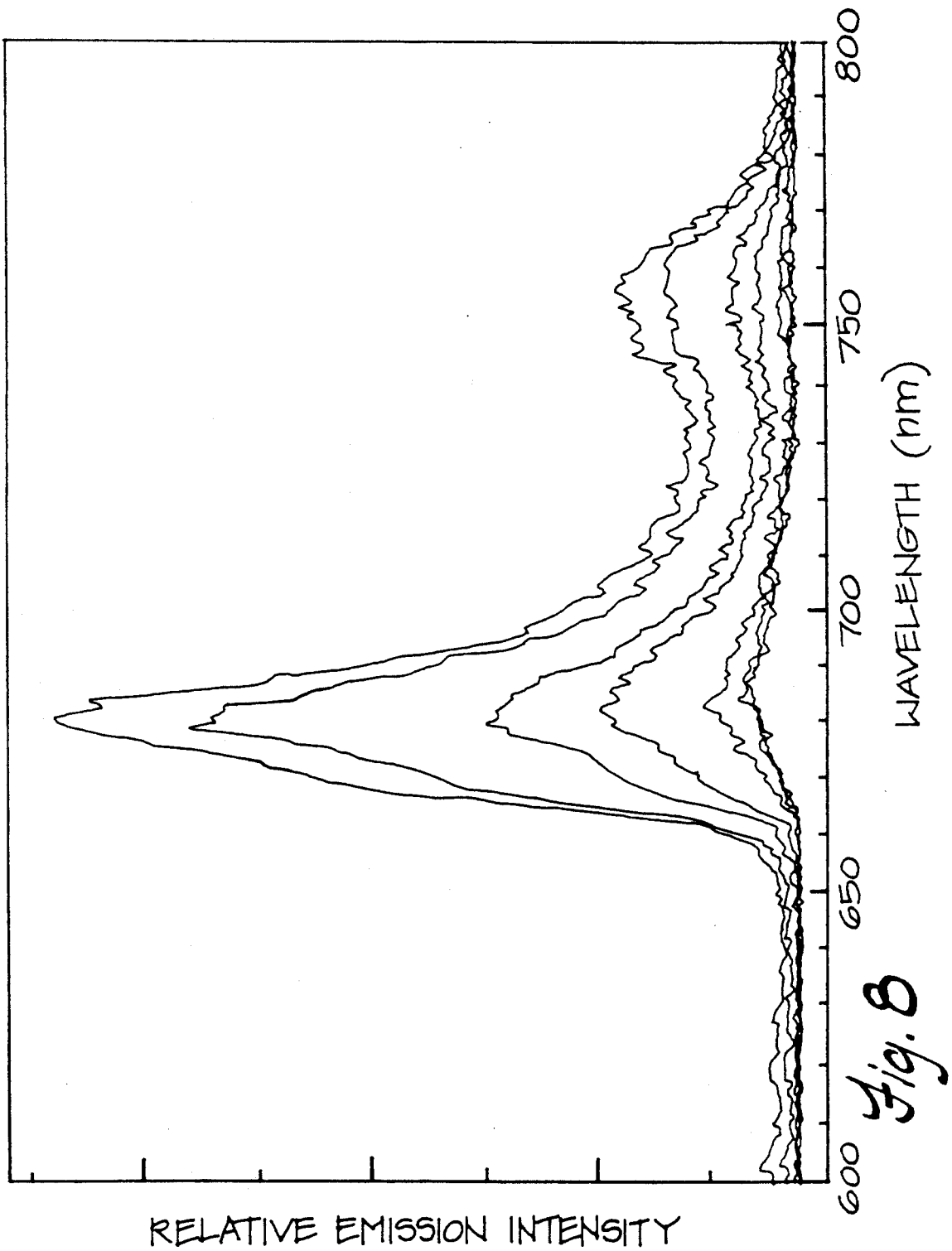
FIG. 8 shows the emission spectrum of an aqueous (pH 7.3) suspension of sapphyrin 1 in the presence of various concentrations of vesicular stomatitis virus (VSV). The traces show in order of increasing emission intensity, VSV lipid concentrations of 0, 0.01, 0.1, 1, 5, 25 and 50 uM. In all cases the total macrocycle concentration was held constant at 1 uM and photoexcitation was effected at 453 nm.
Figure 9:
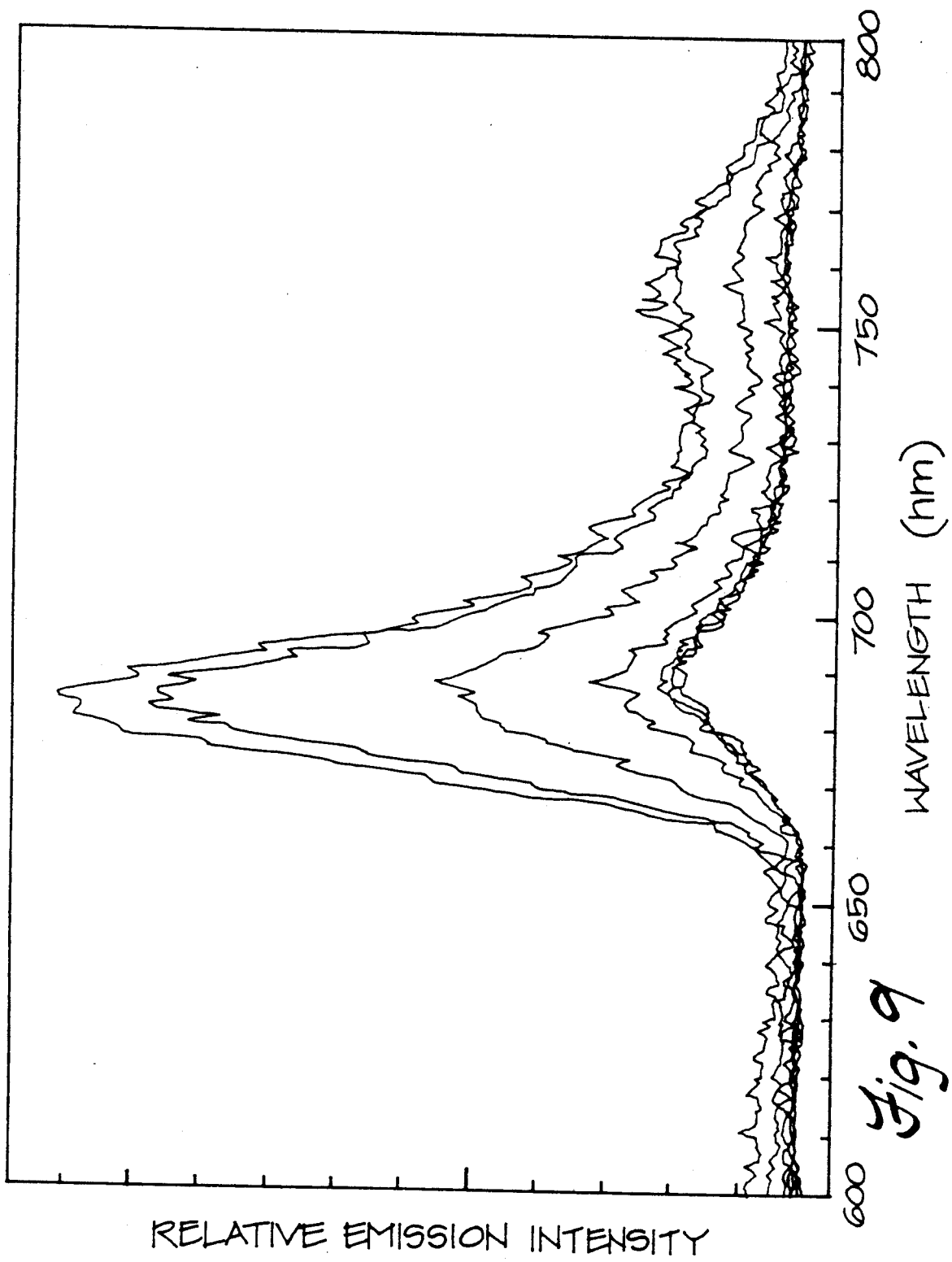
FIG. 9 shows the emission spectrum of an aqueous (pH 7.3) suspension of sapphyrin 2 in the presence of various concentrations of vesicular stomatitis virus (VSV). The traces show in order of increasing emission intensity, VSV lipid concentrations of 0, 0.01, 0.1, 1, 5, 25, and 50 uM. In all cases the total macrocycle concentration was held constant at 1 uM and photoexcitation was effected at 453 nm.

Fluorescence studies on the binding of both sapphyrins 1 and 2 to VSV in PBS, pH=7.3, also were carried out. Fluorescence spectra were obtained with viral lipid concentration varied between 0 and 50 uM with the concentration of each sapphyrin fixed at 1 uM (FIGS. 8 and 9). The observed spectra for both sapphyrins are dominated by monomer-type peaks at 680 and 755 nm and show little evidence for the presence of dimers (as evidenced by the absence of emission signals at 712 nm).

Figure 10:
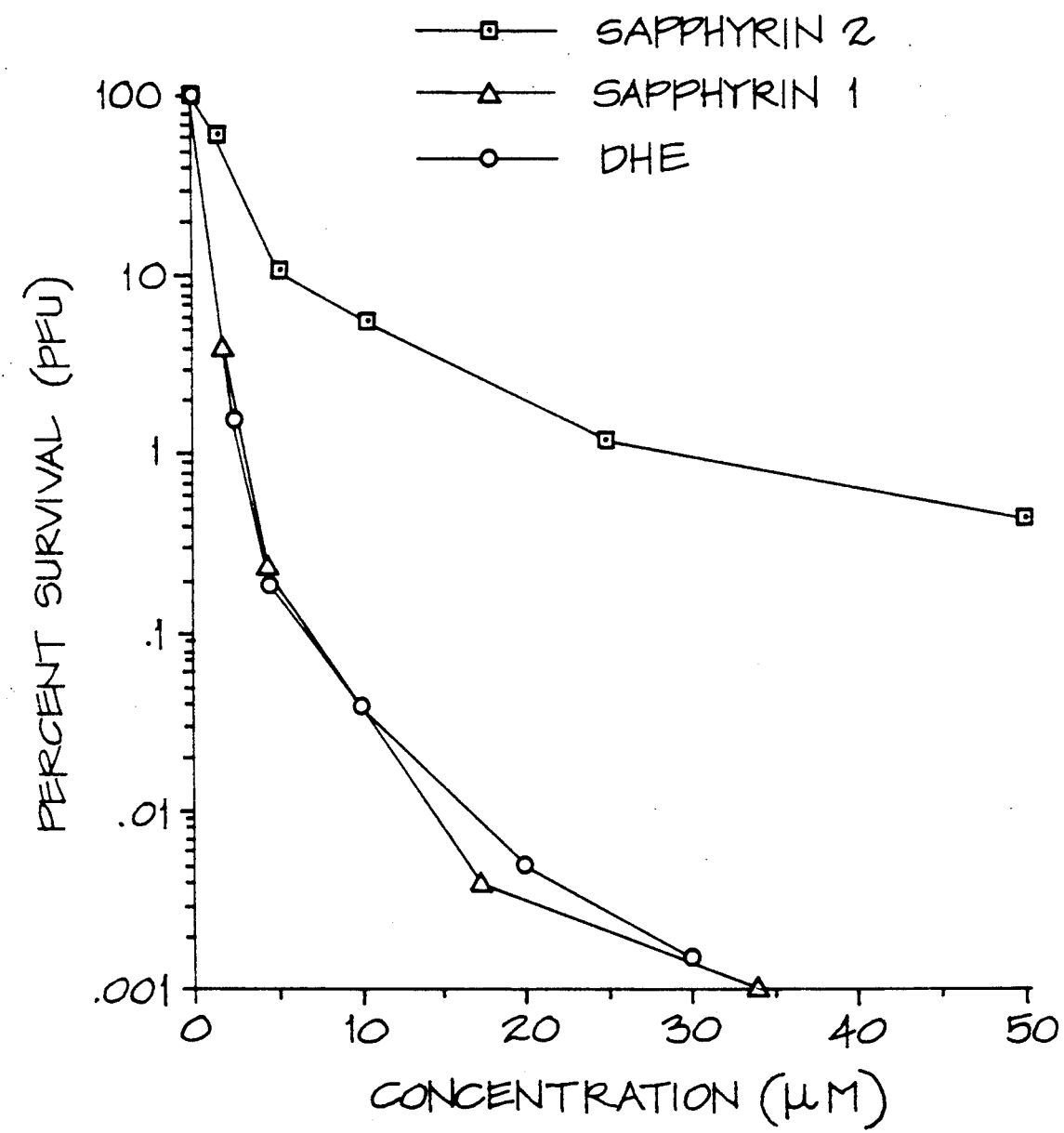
FIG. 10 shows the plot of photodynamic inactivation (PDI) of herpes simplex (HSV-1). The percentage survival (Y-axis) is plotted as a function of the concentration of sapphyrins 1 and 2. Also shown for comparison are the results of an earlier reported HSV-1 PDI effected with dihematoporphyrin ether (DHE) (Skiles, H., Judy, M. M., Newman, J. T. (1987) "Photodynamic inactivation of viruses with hematoporphyrin derivatives", *Abstr. of 6th Southern Biomedical Engineering Conference*, 1987, 83); Matthews, J. L., Sogandares-Bernal, F., Judy, M. M., Marengo-Rowe, A. J., Skiles, H., Leveson, J., Chanh, T., and Newman, J. (1988) "Photodynamic inactivation of human immunodeficiency virus in human blood", *Transfusion*, 28(S), 31S). In all cases, photoirradiation was at a fluence of 10 $J/cm^2$ and was carried out at 680 nm and for the DHE control, excitation was effected at 630 nm. The points shown are the means of at least three separate experiments carried out under identical conditions, which in all cases were found in individual cases to vary by less than 20%.

Survival of HSV-1 infectivity following photodynamic treatment of both static and flowing viral suspensions containing various concentrations of sapphyrin 1 and 2 is shown in FIG. 10. In both studies, the light fluence was held constant at 10 $J/cm^2$ while the sapphyrin concentrations were varied between 4.7 and 33.3 uM. HSV-1 survival data versus DHE photosensitization at 630 nm obtained previously (Skiles, H., Judy, M. M., Newman, J. T. (1987) "Photodynamic inactivation of viruses with hematoporphyrin derivatives", *Abstr. of 6th Southern Biomedical Engineering Conference*, 1987, 83, 85) are also shown for comparison.

Figure 11:
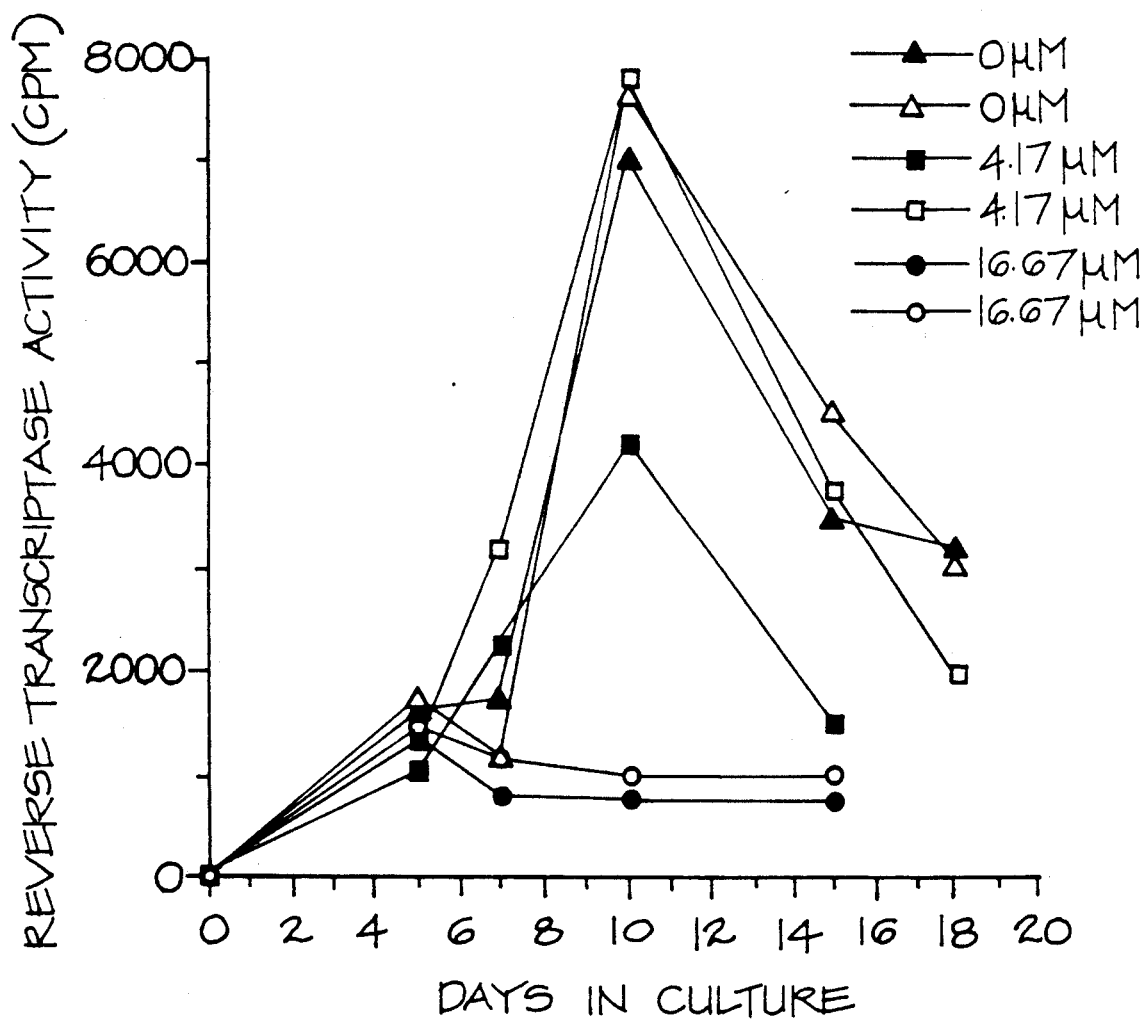
FIG. 11 shows the inactivation of cell-free human immunodeficiency virus (HIV-1) effected using varying concentrations of decaalkyl sapphyrin in the presence (closed points) and absence (open points) of light. Photoexcitation was effected at 10 $J/cm^2$ at 680 nm in a standard flow cell and HIV activity monitored from culture supernatants after inoculation into the human CEM T cell line A.301 using a standard reverse transcriptase assay.
Figure 12:
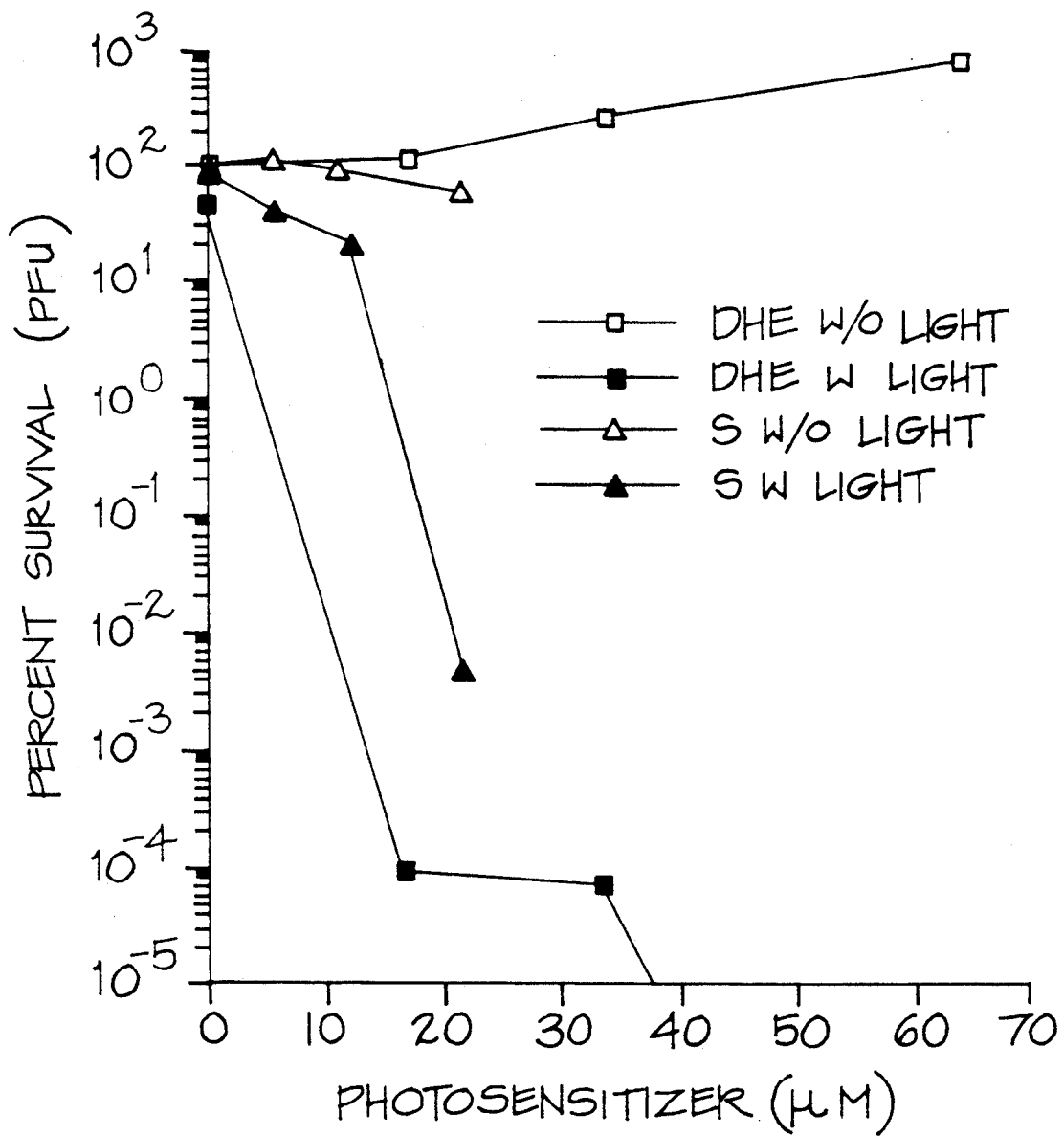
FIG. 12 shows the inactivation of uninfected H9 cells in the presence (closed points) and absence (open points) of light. The same per macrocycle concentrations of decaalkyl sapphyrin (S) and DHE were used. For the sapphyrin, photoexcitation was carried out at 680 nm and for DHE at 630 nm; the light fluence was 10 $J/cm^2$.

The data plotted in FIG. 11 show that 3,8,12,13,17,22-hexaethyl-2,7,18,23-tetramethylsapphyrin is an effective photosensitizer for the photoeradication of cell-free HIV-1. At a concentration of 4 um, and a light fluence of 10J/$cm^2$, this substance effects a 50% photo-killing of HIV-1 judged by standard reverse transcriptase assay, without any apparent dark toxicity. At a concentration of 16 uM, this same material effects a complete photo-killing of the AIDS virus. At this latter concentration, however, there is also evidence of significant dark toxicity with regard to the transformed H9 leukocytes used for the cell line. However, this dark toxicity is limited to the HIV-infected H9 cells; in a critical series of parallel control studies, it was found that neither the decaalkyl sapphyrin compound nor DHE is cytotoxic against uninfected H9 cells in the absence of light at concentrations <20 uM, but that both compounds are similarly efficient at achieving light-induced cellular killing, providing between 4 and 5 log-kills as shown in FIG. 12. Thus the observed dark toxicity in the anti HIV-photodynamic inactivation study is not indicative of a general deleterious cytotoxicity and may indicate an as yet poorly understood photon-free anti-HIV-1 activity. These results suggest that the sapphyrin compounds may be effective for the photo-eradication of T-lymphocytes and other virally infected white blood cells, including monocytes. In further control experiments the decaalkyl sapphyrin compound showed no significant dark or light cytotoxicity against normal, non-leukocytic cellular components, and was found to have an $LD_{50}$ in mice of about 10–20 mg/kg. Thus, in terms of both efficacy and general toxicity there is a well-defined therapeutic window for the use of the compound in blood purification procedures. Even at the highest anticipated dosages of 16 uM, a toxicological safety factor of between 75 and 150 might be expected to pertain.

In summary, it is shown that sapphyrin compounds act as photosensitizers for the inactivation of several enveloped viruses, including HSV-1 and HIV-1. Results of fluorescence spectral studies suggest that sapphyrin monomers bind to the viral envelope. Prior photophysical observations of sapphyrin 1 (Maiya, B. G., Cyr, M., Harriman, A., and Sessler, J. L. (1989) "In-vitro photodynamic activity of diprotonated sapphyrin: a 22 pi-electron pentapyrrolic porphyrin-like macrocycle", (Submitted to *J. Phys. Chem.*), include $O_2(^1Delta-g)$ generation of excited triplet monomers. This observation and that of Grossweiner and Goyal (Grossweiner, L. L., Blum, A., Goyal, G. C. (1985) "Photophysics and photochemistry of hematoporphyrin, hematoporphyrin derivative and uroporphyrin I", *Adv. Exp. Med. Biol.* 193, 181–192) that the dominant mechanism of photosensitized damage to phospholipid-containing liposomes using HPD at comparable macrocycle concentrations was attacked by $O_2(^1Delta-g)$ generated by bound monomers suggest that the light-induced viral inactivation was, in significant part, photodynamic in nature.

Our fluorescence emission studies of sapphyrins 1 and 2 summarized in FIGS. 3 through 9 strongly suggest that monomers of both compounds bind to the viral envelope. Comparisons of the fluorescence emission of sapphyrin 1 observed in the presence of liposomes containing both PCC and C (FIGS. 5 and 6) with that observed in the presence of intact, cell-free VSV (FIG. 8) suggest that the sapphyrin binding is within the lipid bilayer region of the viral envelope. The foregoing observations argue that the observed photosensitized inactivation of HSV-I with sapphyrin 1 is photodynamic, arising from generation of $O_2(^1Delta\text{-g})$ by excited triplet static monomers bound within cholesterol-rich regions of the lipid region of the viral envelope. Moreover, the dominance of fluorescence emission at 680 nm, compared to that at 712 nm in liposomes of higher C/P value (e.g. >0.61), suggests that the sapphyrin localizes preferably in the cholesterol-rich regions of the lipid component of the viral envelope. A number of other studies support this model. Various porphyrins, which are derivable from protoporphyrin and have large hydrophobic ring regions, have demonstrated a tendency to bind to liposomal membranes and to the lipid regions of cell membranes (Ehrenberg, B., Malik, Z., and Nitzan, Y. (1985) "Fluorescence spectral changes of hematoporphyrin derivative upon binding to lipid vesicles, *Staphylococcus aureus* and *Escherichia coli* cells" *Photochem. Photobiol.* 41, 429–435. Also, significant correlation between cell membrane localization and photosensitized membrane damage has been shown for porphyrin monomers of HPD (Kessel, D. (1977) "Effect of photoactivated porphyrins at the cell surface of leukemia L1210 cells", *Biochemistry* 16 3443–3449; Dubbelman and van Stevemirete, T., and van Steveninck, J. (1984) "Photodynamic effects of hematoporphyrin-derivative on transmembrane transport systems of murine L929 fibroblasts", *Biochim. Biophys. Acta* 771, 209–217; Ehrenberg, B., Malik, Z., and Nitzan, Y. (1985) "Fluorescence spectral changes of hematoporphyrin derivative upon binding to lipid vesicles, *Staphylococcus areus* and *Escherichia coli* cells", Photochem Photobiol. 41, 429–435) for MC, and early in cell loading, for CE (Kessel, D. (1989) "Determinants of photosensitization by mono-L-aspartyl chlorin e6", *Photochem. Photobiol.* 49, 447–452). All of these compounds possess large hydrophobic macrocycles with their ring boundaries having relatively apolar substituents. Furthermore, Lytle et al. (Lytle, C. D., Carney, P. G., Felten, R. P., Bushar, H. F., and Straight, R. C. (1989) "Inactivation and mutagenesis by photodynamic treatment with therapeutic dyes", *Photochem. Photobiol.* 49S, 76S) recently reported that photodynamic inactivation of HSV-1 using HPD was not mutagenic to the virus. This result argues for photochemical attack of regions excluding the viral DNA, but including the viral envelope. Further implication of damage to the viral envelope is found in the study of Schnipper, et al. (Schnipper, L. E., Lewin, A. A., Swartz, M., and Crumpacker, C. S. (1980) "Mechanisms of photodynamic inactivation of herpes simplex viruses", *J. Clin. Invest,* 65, 432–438) in which HPD photosensitization of HSV-1 prevented binding and internalization of the virus into the host cell.

In contrast with our results supporting the implication of monomers of sapphyrin I in photodynamic inactivation of HSV-1 bound to C-rich regions of the viral envelope, our fluorescence studies of sapphyrin 2 suggest that more polar regions of the envelope are involved in macrocycle binding. However, our fluorescence spectra support the presence of monomers of the compound as the dominant bound species. The fluorescence emission spectrum of sapphyrin 2 in the presence of VSV (FIG. 9) suggests that monomers are the dominant fluorescent species which bind to the viral envelope. Comparison of the position of the emission maximum located near 690 nm with that for sapphyrin 2 in SDS (692 nm; cf. FIG. 7) further suggests that monomers of the compound bind to relatively more polar regions of the viral envelope than does the decaalkylsapphyrin 1. Possible regions include the phospholipid-rich regions of the envelope membrane, perhaps near the surface where the charged head groups are located. The less polar cholesterol-regions probably are excluded.

Examination of FIG. 10 shows that sapphyrin 1 is a potential photosensitizer of HSV-I inactivation with efficiency on a per macrocycle basis comparable to that obtained with the more-studied DHE, whereas the photosensitizing efficiency of sapphyrin 2 is significantly less than that evidenced by the decaalkylsapphyrin 1.

Sapphyrin 1 is significantly better than DHE, however, for the inactivation of cell-free HIV-1. Sapphyrin 1 is twice as effective on a normalized per macromolecule incident unit of light basis compared to with DHE. Fifty % photo-killing of HIV-1 occurs at a concentration of 4 uM and 100% at 16 uM, as indicated in FIG. 11. Although there is evidence of dark toxicity toward the transformed CEM T cells, A301, an eternalized, cancerous strain of human T4 lymphocytes, the dark toxicity appears limited to the HIV-1 infected cells. No cytotoxicity is observed in uninfected H9 cells, another eternalized T lymphocyte cell line, at concentrations of Sapphyrin 1 or DHE of <20 uM in the absence of light (FIG. 12).

Fluorescence data suggest that both sapphyrins bind as monomers to the viral envelope. It appears that the large difference observed in efficiency of viral photodynamic inactivation arises because of different binding environments. Such an effect may manifest, for example, in such ways as differences in binding concentrations of photosensitizer, effects of local environment on ($O_2(^1Delta\text{-g})$) yield, and in the identity of available oxidizable substrate.

The efficient photodynamic inactivation of HIV-1 and HSV-1 using decaalkyl sapphyrin indicates the usefulness of this efficient photodynamic agent for inactivation of infectious agents, especially envelope viruses, in human blood and blood products.

On a per molecule basis, sapphyrin 1 is as effective as DHE for anti-HSV-1 and anti-HIV-1 photodynamic inactivation. But in the context of a blood purification protocol, sapphyrin 1 is significantly more efficient on a per unit of incident light basis than is DHE. DHE absorbs at 630 nm while sapphyrin 1 absorbs at 680 nm. Where a 1 mm path is used in a fluor-based blood purification, this difference in absorbtivity results in an efficiency difference of approximately 1.8. Due to Beer's law-like nature of blood (A. J. Welch, G. Yoon, and M. J. C. van Gemert, *Lasers Surg. Med.,* 6, 488–493, 1986), this efficiency enhancement would be exponentially enhanced if a longer light path were employed.

What is claimed is:

1. A method of photodynamic inactivation of infectious agents, comprising:

forming a mixture by adding a decaalkylsapphyrin or a dicarboxy functionalized decaalkylsapphyrin compound to a fluid comprising infectious agents; and subjecting said mixture to irradiation with light at a wavelength at or near the absorption maximum of said decaalkylsapphyrin or dicarboxy functionalized decaalkylsapphyrin compound for a time and at an intensity sufficient to inactivate said infectious agents.

2. The method of claim 1 wherein the decaalkylsapphyrin compound is 3,8,12,13,17,22-hexaethyl-2,7,18,23-tetramethylsapphyrin.

3. The method of claim 1 wherein the dicarboxy functionalized decaalkylsapphyrin compound is a dicarboxy-functionalized analog of 3,8,12,13,17,22-hexaethyl-2,7,18,23-tetramethylsapphyrin.

4. The method of claim 1 wherein the dicarboxy functionalized decaalkylsapphyrin compound is 8,17-bis(carboxymethyl)-3,12,13,22-tetraethyl-2,7,18,23-tetramethylsapphyrin.

5. The method of claim 1 wherein the wavelength is between about 600 nm and 700 nm.

6. The method of claim 1 wherein the wavelength is about 680 nm.

7. The method of claim 1 wherein the light is provided by a laser.

8. The method of claim 1 wherein the irradiation is at an intensity of from about 20 mW/cm$^2$ to about 50 mW/cm$^2$.

9. The method of claim 1 wherein the irradiation results in an exposure of the mixture to 10 Joules/cm$^2$.

10. The method of claim 1 wherein the the decaalkylsapphyrin or dicarboxy functionalized decaalkylsapphyrin compound in the mixture is at a concentration between about 4 uM and 35 uM.

11. A method of photodynamic inactivation of viruses or retroviruses, comprising:

obtaining a viral or retroviral suspension in a fluid;

adding a decaalkylsapphyrin or a dicarboxy functionalized decaalkylsapphyrin compound to said suspension; and irradiating said suspension with light at a wavelength at or near the visible absorption maximum of said decaalkylsapphyrin or dicarboxy functionalized decaalkylsapphyrin compound for a time and at an intensity sufficient to effect inactivation of virus or retrovirus in said suspension.

12. The method of claim 11 wherein the wavelength is 680 nm.

13. The method of claim 11 wherein the intensity sufficient to effect the inactivation is about 20 mW/cm$^2$ to about 40 mW/cm$^2$.

14. The method of claim 11 wherein the irradiating sufficient to effect the inactivation is in an amount of about 10 J/cm$^2$.

15. The method of claim 11 wherein the viral or retroviral suspension comprises cytomegalovirus, hepatitis virus type B; non-A, non-B hepatitis virus, human lymphotrophic virus type 1, human immunodeficiency virus type 1, simian immunodeficiency virus, or herpes simplex virus type 1.

16. The method of claim 11 wherein the viral or retroviral suspension comprises a membranous enveloped virus.

17. The method of claim 11 wherein the decaalkylsapphyrin compound is 3,8,12,13,17,22-hexaethyl-2,7,18,23-tetramethylsapphyrin.

18. The method of claim 11 wherein the dicarboxy functionalized decaalkylsapphyrin compound is 8,17-bis(carboxymethyl)-3,12,13,22-tetraethyl-2,7,18,23-tetramethylsapphyrin.

19. The method of claim 11 wherein the fluid is blood or a blood product.

20. A method of photodynamic inactivation of enveloped viruses or retroviruses in blood, comprising:

circulating virus-containing or retrovirus-containing blood through a transparent tube arranged in multiple planar loops;

adding a decaalkylsapphyrin or a dicarboxy functionalized decaalkylsapphyrin compound to said circulating blood; and irradiating said circulating blood at a wavelength of about 680 nm.

21. The method of claim 20 wherein the decaalkylsapphyrin compound is 3,8,12,13,17,22-hexaethyl-2,7,18,23-tetramethylsapphyrin.

22. The method of claim 20 wherein the dicarboxy functionalized decaalkylsapphyrin compound is 8,17-bis(carboxymethyl)-3,12,13,22-tetraethyl-2,7,18,23-tetramethylsapphyrin.

23. A method of photodynamic deactivation of infectious agents in a fluid, comprising:

mixing a decaalkylsapphyrin or a dicarboxy functionalized decaalkylsapphyrin compound with a fluid to be purified;

irradiating said fluid at a wavelength at or near the absorption maximum of said decaalkylsapphyrin or dicarboxy functionalized decaalkylsapphyrin compound at an intensity and for a period of time sufficient to inactivate one or more infectious agents that may be present in said fluid.

24. The method of claim 23 wherein said fluid is irradiated at a wavelength of about 680 nm.

25. The method of claim 23 wherein the irradiating is at an energy of about 10 J/cm$^2$.

26. The method of claim 23 wherein the decaalkylsapphyrin or dicarboxy functionalized decaalkylsapphyrin compound in the fluid is at a concentration of about 4 uM to about 35 uM.

27. The method of claim 23 wherein the dicarboxy functionalized decaalkylsapphyrin compound is 8,17-bis(carboxymethyl)-3,12,13,22-tetraethyl-2,7,18,23-tetramethylsapphyrin.

28. The method of claim 23 wherein the fluid is further characterized as being blood.

29. The method of claim 23 wherein the fluid is further characterized as being a blood product.

30. The method of claim 23 wherein the infectious agent is a virus or retrovirus.

31. The method of claim 30 wherein the virus or retrovirus is further characterized as having an envelope.

32. The method of claim 30 wherein the virus or retrovirus is characterized as being cytomegalovirus, hepatitis virus type B; non-A, non-B hepatitis virus, human lymphotrophic virus type 1, human immunodeficiency virus type 1, simian immunodeficiency virus, Epstein barr virus, or herpes simplex virus type 1.

33. The method of claim 23 wherein the infectious agent is *Tympanosoma cruzi* or *malaria plasmodium*.

* * * * *

UNITED STATES PATENT AND TRADEMARK OFFICE
CERTIFICATE OF CORRECTION

PATENT NO. : 5,041,078
DATED : August 20, 1991
INVENTOR(S) : Matthews et al.

It is certified that error appears in the above-identified patent and that said Letters Patent is hereby corrected as shown below:

In column 1, line 18, before BACKGROUND OF THE INVENTION insert a new paragraph:

--This invention was made in part with government support under the National Science Foundation Presidential Young Investigator Award (1986) to J.L. Sessler, grant CHE-8552768. The government has certain rights in the invention.--

Signed and Sealed this

Twenty-first Day of September, 1993

Attest:

BRUCE LEHMAN

*Attesting Officer*  *Commissioner of Patents and Trademarks*